United States Patent
Litzenberg et al.

(10) Patent No.: US 7,543,500 B2
(45) Date of Patent: Jun. 9, 2009

(54) METHOD AND APPARATUS FOR NON-DESTRUCTIVE TESTING OF COMPONENTS OF GAS TURBINE ENGINES MADE OF MONOCRYSTALLINE MATERIALS

(75) Inventors: Holger Litzenberg, Rangsdorf (DE); Heike Floege, Zossen (DE); Jochen Scholz, Zeuthon (DE); Anthony K. Dunhill, Bristol (GB)

(73) Assignee: Rolls-Royce Deutschland Ltd & Co KG, Blankenfelde-Mahlow (DE)

( * ) Notice: Subject to any disclaimer, the term of this patent is extended or adjusted under 35 U.S.C. 154(b) by 168 days.

(21) Appl. No.: 11/584,763

(22) Filed: Oct. 23, 2006

(65) Prior Publication Data

US 2007/0157733 A1   Jul. 12, 2007

(30) Foreign Application Priority Data

Oct. 21, 2005   (EP) .................................. 05109851

(51) Int. Cl.
*G01N 29/04* (2006.01)

(52) U.S. Cl. .............................. 73/593; 73/620; 73/660

(58) Field of Classification Search .................. 73/602, 73/593, 587, 599–600, 618–622, 625–630, 73/632–633, 659–660
See application file for complete search history.

(56) References Cited

U.S. PATENT DOCUMENTS 5,275,052 A * 1/1994 Luttrell et al. ................. 73/619
5,696,324 A   12/1997 Tsuboi
5,942,690 A * 8/1999 Shvetsky ..................... 73/660
6,082,198 A * 7/2000 Sabourin et al. ............. 73/633
6,487,909 B2 * 12/2002 Harrold et al. ................ 73/593

FOREIGN PATENT DOCUMENTS

GB   2 285 129 A   6/1995

OTHER PUBLICATIONS

A. Minachi; P.D. Panetta; S. Nakahama: "Turbine blades inspection using high frequency ultrasonic technique" AIP Conference proceedings 2001, vol. 557, 2001, pp. 1634-1641, XP002373816.
H.D.Mair; P. Ciorau; D. Owen; T. Hazelton; G. Dunning: "Ultrasonic simulation- Imagine3D and Simscan: Tools to solve the inverse problem for complex turbine components" AIP Conference Proceedings 2000, vol. 509, 2000, pp. 911-917, XP002373817.

* cited by examiner

*Primary Examiner*—Helen C. Kwok
(74) *Attorney, Agent, or Firm*—Timothy J. Klima

(57) ABSTRACT

Single-crystal components of gas turbine engines, like turbine blades, are inspected in the installed state within the engine for cracking in certain critical areas using longitudinal ultrasonic waves. A first, rough orientation of the ultrasonic waves onto the critical area is accomplished under camera-visual control using an ultrasonic probe whose shape conforms to the respective component area and which, therefore, can be form-fitted to the component. For fine-positioning of the ultrasonic waves in the critical area, a reference signal is generated at a component-specific geometrical contour adjacent to the critical area by second ultrasonic waves emitted at a local distance to the first ultrasonic waves. The presence of this signal ensures the safe, disturbance-free detection of cracks in the critical blade area by means of longitudinal sonic waves. The invention includes an apparatus for the performance of the method.

15 Claims, 4 Drawing Sheets

Figure 1:
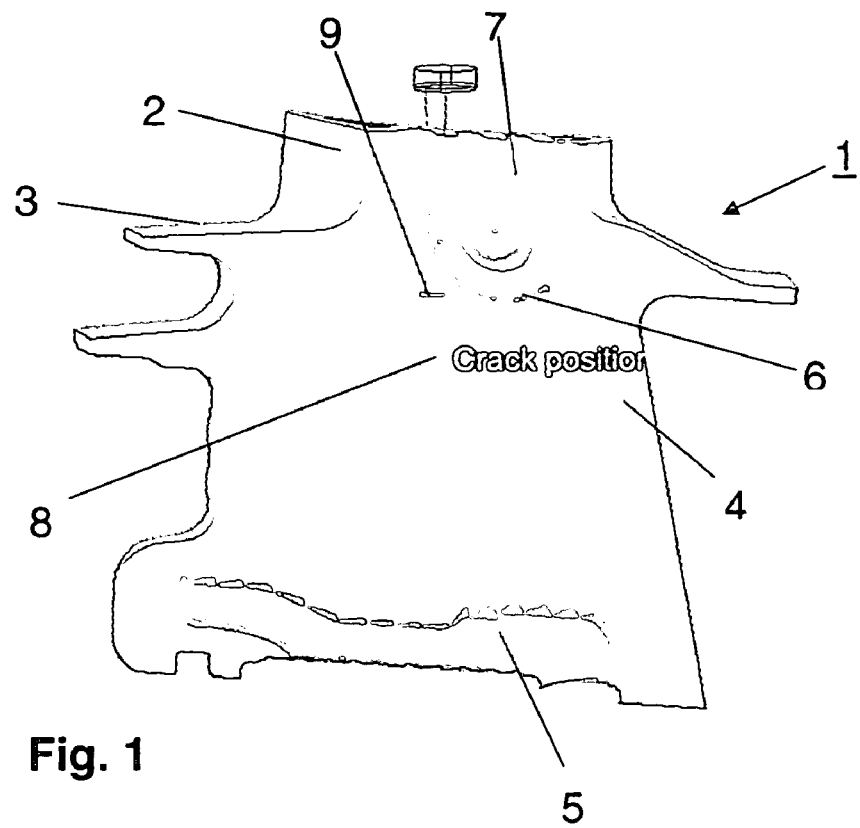

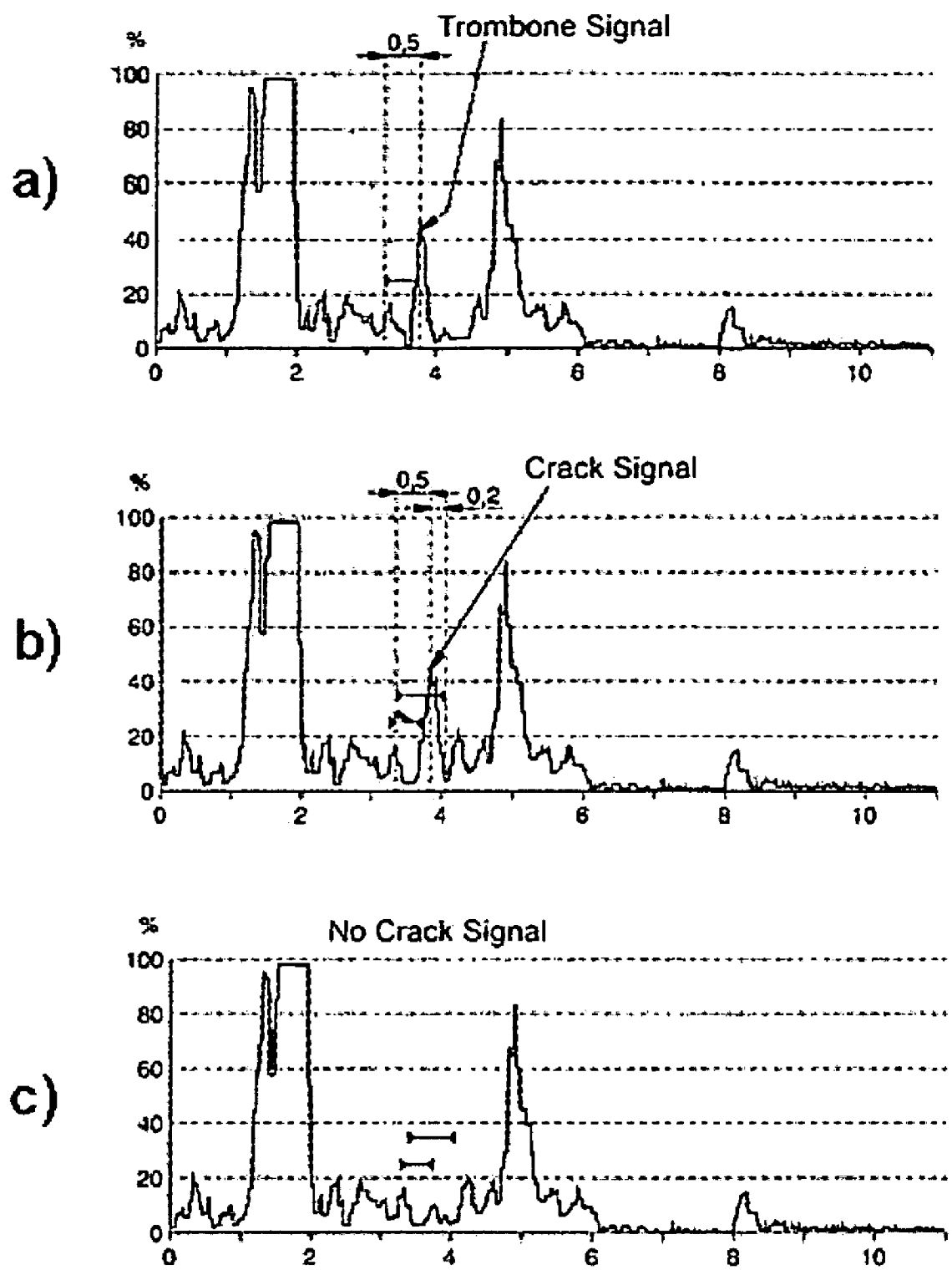
Fig. 7a-c

METHOD AND APPARATUS FOR NON-DESTRUCTIVE TESTING OF COMPONENTS OF GAS TURBINE ENGINES MADE OF MONOCRYSTALLINE MATERIALS

This application claims priority to European Patent Application EP05109851.5 filed Oct. 21, 2005, the entirety of which is incorporated by reference herein.

BACKGROUND OF THE INVENTION

This invention relates to a method for non-destructive testing of components of gas turbine engines made of monocrystalline materials for the presence of cracks in a certain, critical component area upon expiry of a specific operating time, and in particular, for the inspection of turbine blades. Moreover, this invention relates to an apparatus for the performance of said method.

Non-destructive material testing using ultrasound for the detection of shrinkage, cracks and other flaws in the interior of a component has been known for quite a long time. The ultrasonic waves produced by the quartz oscillator of an ultrasonic probe positioned on the workpiece surface are transmitted into the component via a couplant. While—on a flawless component—the ultrasonic waves are reflected at the opposite bottom surface, return to the quartz oscillator now acting as receiver and produce a bottom echo, reflection at a discontinuity in the component results in a flaw signal which differs from the bottom echo. The shape of the flaw echo displayed on a screen enables the size, depth and type of the defect to be determined by comparing it with the bottom echo.

Inspection of components made of monocrystalline materials is, however, problematic since transverse ultrasonic waves are reflected differently on monocrystals, depending on the respective crystallographic orientation, as a result of which the signal reflected by a crack actually present in the component will not be reliably received and the discontinuity not safely detected.

In addition, ultrasonic inspection of monocrystalline components is difficult if the particular geometry of a component area to be flaw-tested leads to disturbance signals, as a result of which the reliability of the inspection is not ensured. Flaw detection is particularly problematic and costly if the components to be inspected are installed in a fixture and have to be removed for non-destructive testing and re-installed afterwards.

It is known of the blades of gas turbine engines, for example, that they may develop cracks in a certain area of the blade root. At certain intervals, it is therefore advisable to crack-inspect all turbine blades in question in a test laboratory by non-destructive methods. Apart from the high disassembly and assembly effort, the known methods and apparatuses are not capable of detecting, or excluding, crack formation in the interior of the blades in certain critical areas in a quick, safe and simple way. The sensitivity of X-rays used for this purpose is not sufficient to detect cracks in the interior of the turbine blades. Fluorescent inspection, as another well-known inspection method is, however, only suitable for the detection of superficial cracks.

DESCRIPTION OF THE INVENTION

The present invention, in a broad aspect, provides an inspection method and an inspection apparatus for components made of monocrystalline materials, and in particular, for crack inspection of turbine blades of gas turbine engines, which ensure a meaningful, safe inspection of the components with a minimum time investment.

It is a particular object of the present invention to provide a solution to the above problems by a method in accordance with the features described herein and by an inspection apparatus designed in accordance with the features also described herein. Further features and advantageous embodiments of the present invention will be apparent from the present description.

An essential inventive feature is that the inspection of components made of monocrystalline materials by longitudinal ultrasonic waves is performed within the engine, i.e., in the installed state of the components. It was found that it is possible to obtain reliable, sufficiently intense, disturbance-free reflection signals on monocrystals, despite the different crystal orientation in the respective components. In accordance with another important feature of the present invention, precise positioning of the probe transmitting the ultrasonic waves and receiving the reflected signals, an operation which is extremely difficult to be performed within the engine, is accomplished under camera-visual control, with the outer contours of the probe conforming exactly to the outer contour of the component in the area in which the inspection is to be performed so that the probe is virtually form-fitted to the respective area of the component and pre-positioned, at least roughly.

Since a reliable, disturbance-free reflection signal from a crack (flaw signal) is only obtainable if the longitudinal ultrasonic waves are emitted to the critical inspection area from a specific position and direction, additional ultrasonic waves for precise positioning of the probe are emitted at a local distance to the ultrasonic waves for crack detection, i.e., for precise orientation of the latter. These additional ultrasonic waves for fine-positioning of the probe are emitted at a place which corresponds to a contour which, at a defined distance to the critical area, is present within the component. Only a reference signal (for example a trombone signal) reflected by this component-specific contour ensures that the inspection waves are emitted from the correct position into the correct direction and an existing crack is actually detected.

The method according to the present invention enables a great variety of components, for example the blades of the high-pressure turbine, to be quickly and safely inspected at short intervals with minimum assembly effort and cost investment.

One feature of the apparatus for the performance of the method according to the present invention is a specially designed positioning probe for the positionally correct emission of the longitudinal ultrasonic waves for the detection of cracks in a certain—critical—area of the components. For rough-positioning, the probe is provided with an outer contour which conforms to the component in the area to be inspected, enabling the probe to be readily form-fitted at a certain position on the component. For fine-positioning, a further quartz oscillator element for provisioning of a reference or positioning signal is arranged at a defined distance to the quartz oscillator element for the generation of the ultrasonic waves for crack detection, this reference signal being reflected at an inner contour present in the component at a defined distance to the critical area.

In accordance with a further important feature of the present invention, a miniature camera is allocated to the positioning probe to provide visual control of probe manipulation, with the miniature camera and the probe being connected to a flexible manipulation element (manipulator) at whose outer end located outside of the engine are arranged a control unit for moving the probe or the miniature camera, respectively, and, in the one case, a signal indicator unit with change-over switch for displaying the reference signal or, if applicable, a generated flaw signal and, in the other case, a screen for monitoring the probe manipulation movements.

In accordance with another important feature of the present invention, a supply line is attached to the flexible manipulator for the miniature camera to apply couplant to that area of the component at which the ultrasonic waves are transmitted into the monocrystalline material. Outside of the engine, the supply line enters a metering container filled with couplant with a metering piston that can be actuated by a screw spindle. Thus, the couplant can be metered manually under visual control and applied positionally correct—also for marking defective components.

Figure 3:
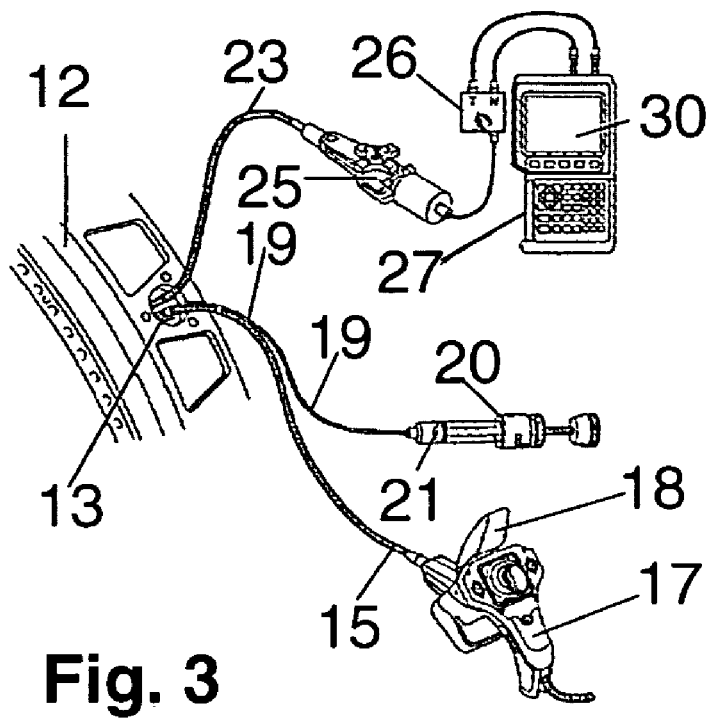
Figure 4:
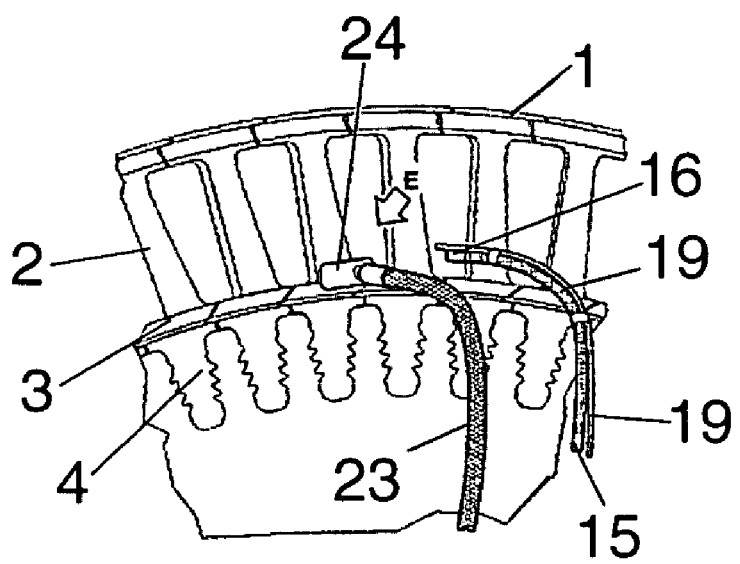
Figure 5:
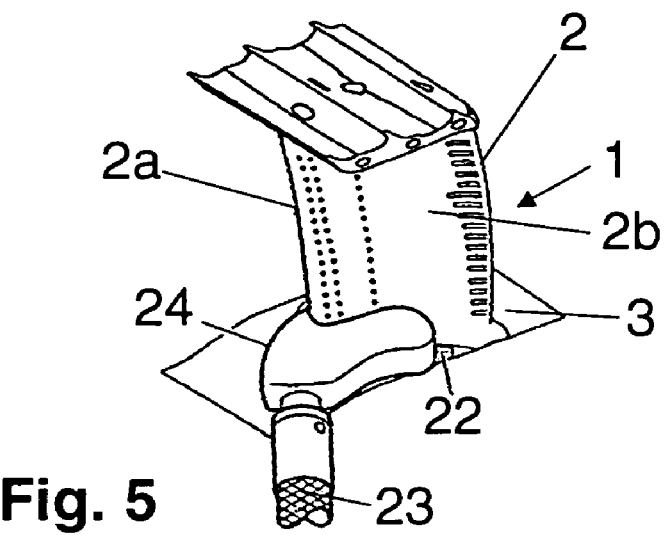
Figure 6:
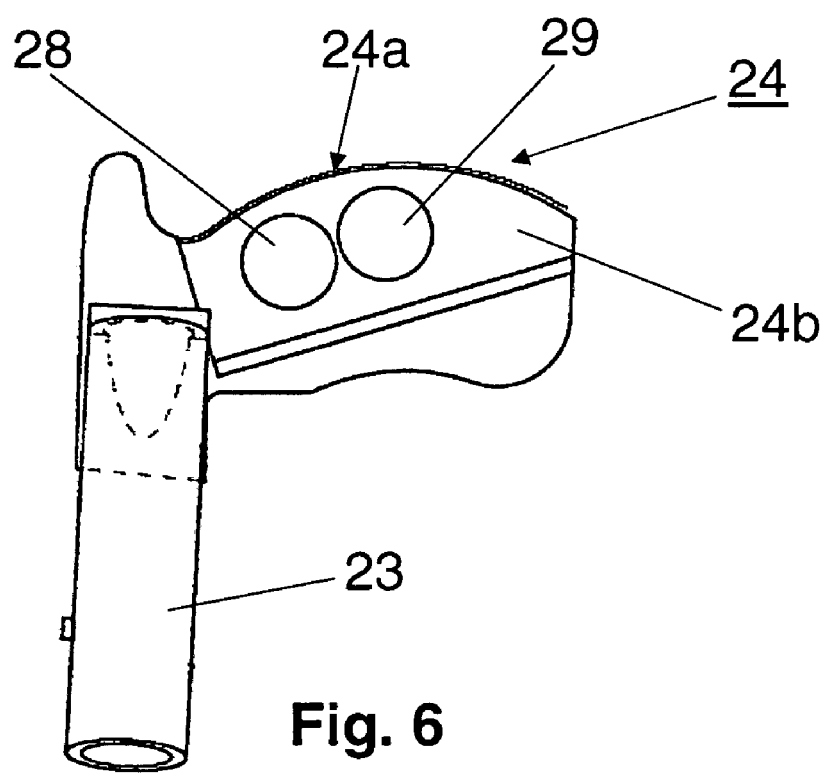

The present invention is more fully described in the light of the accompanying drawings showing a preferred embodiment. In the drawings, FIG. 1 is a sectional view in the area of the platform and the root of a turbine blade, FIG. 2 is a partial view of the engine and of the inspection apparatus arranged in the area of the combustion chamber and the high-pressure turbine, FIG. 3 is a view of the components of the inspection apparatus that are located outside of the engine, FIG. 4 is an enlarged representation of the inspection apparatus in the area of the turbine blades to be inspected, FIG. 5 is a view of a turbine blade with a positioning probe attached to it for the performance of the inspection, FIG. 6 is an underside view of the probe with the two quartz oscillator elements, and FIGS. 7a-c show three ultrasonic measuring graphs, in which a) the reference signal, b) crack signal and c) no crack signal, can be recognized.

FIG. 1 shows, in longitudinal sectional view, the bottom part of a turbine blade 1 with an airfoil 2, a platform 3 and a blade root 4. A cooling air duct 5 provided in the blade root 4 leads from a so-called trombone edge 6 (edge of a trombone duct) to the cooling ducts 7 provided in the airfoil 2. In the drawing of FIG. 1, a crack-susceptible—critical—area 8 exists on the left-hand side of the trombone edge 6 in which a crack 9 is schematically shown.

Figure 2:
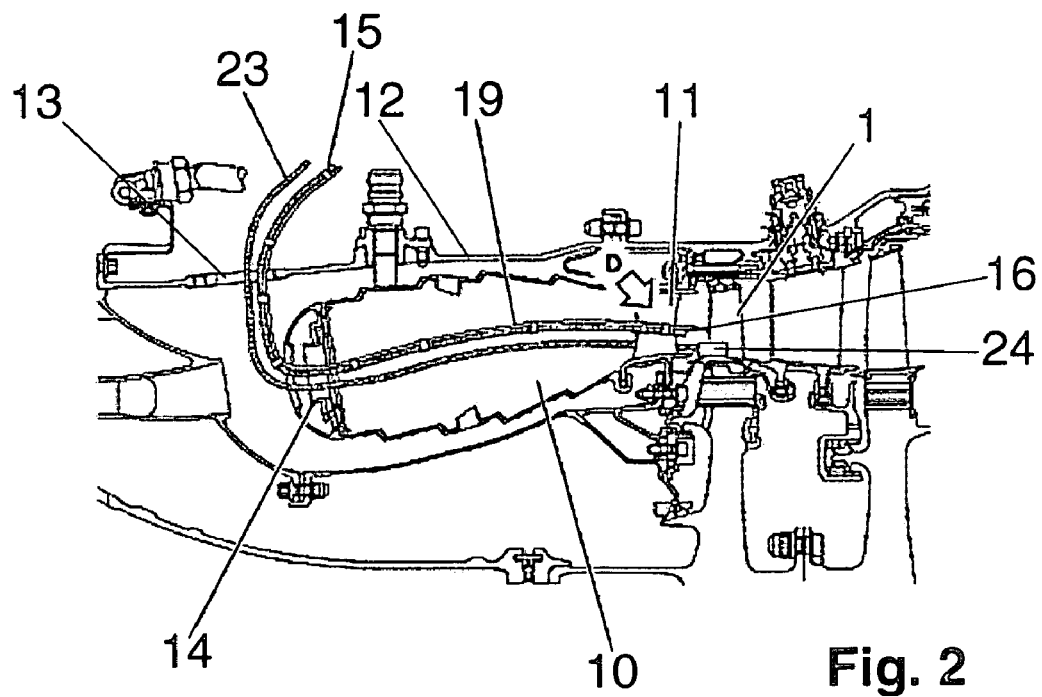

The partial view of a gas-turbine engine in FIG. 2 shows, at the exit of the combustion chamber 10, the stator vanes 11 followed by the above-mentioned high-pressure turbine blades 1 to be inspected. All turbine blades 1 on the rotor can be inspected in the installed state within the engine in the above-mentioned crack-susceptible area using the ultrasonic inspection apparatus described below. For installation of the ultrasonic inspection apparatus, one of the several burners (not shown) is removed from the combustion chamber outer casing 12, enabling the measuring elements required for ultrasonic inspection to be fed through the opening 13 so created in the combustion chamber outer casing 12 and through the burner sleeve 14 up to the respective turbine blade 1. The rotor disk, to which the turbine blades 1 are attached, can be gradually advanced by means of a driving device (not shown), this enabling the individual turbine blades 1 on the rotor disk to be inspected one after the other without removing the ultrasonic inspection apparatus.

A first important element of the ultrasonic inspection apparatus (also refer to FIGS. 3 to 6) is a borescope, i.e. a miniature camera 16 attached to the forward end of a flexible first manipulator 15 which is moveable by means of a first control unit 17 in four degrees of freedom, this control unit 17 being connected to the rearward end of the manipulator 15, and provides a pictorial representation of the area of the respective turbine blade 1 to be investigated on a screen 18 provided on the first control unit 17.

A second important element of the ultrasonic inspection apparatus is a couplant supply line 19 fitted to the first manipulator 15. The forward end of the supply line 19, which—like the miniature camera—is moveable by means of the control unit 17, protrudes beyond the free end face of the miniature camera 16, while the rearward end of the supply line 19 issues into a metering container 20 holding the couplant. In the metering container 20, a manually moveable metering piston 21—here adjustable via a screw spindle by rotation—for finely dosed application of the couplant 22 in the area of inspection on the respective turbine blade 1, is provided.

A third important element of the ultrasonic inspection apparatus is a positioning probe 24 fitted to the forward end of the second manipulator 23. Connected to the rearward end of the second manipulator 23 located outside of the combustion chamber 10 is a second control unit 25 by which the positioning probe 24 can be moved in any desired direction and—via a change-over switch 26—a signal indicator 27 (crack detector) for representation of the signals received from the positioning probe 24.

As shown in FIG. 6, two—first and second—quartz oscillator elements 28 and 29 acting as transmitter and receiver are arranged on the bottom of the positioning probe 24. The quartz oscillator elements 28, 29 are designed for the generation of longitudinal ultrasonic waves. In addition, the positioning probe 24 is designed such that the longitudinal ultrasonic waves for detection of cracks are emitted precisely into that area of the blade root 4 in which cracking is expected and which, therefore, is to be inspected. The probe has a side face 24a which fully fits around the leading edge 2a of the airfoil 2 and the pressure side 2b of the airfoil 2 and a bottom face 24b whose surface contour is completely identical to the surface contour of platform 3 of the turbine blade 2. Thus, the positioning probe 24 can be form-fitted to the airfoil 2 and the platform 3 in a specific position. Also, the two quartz oscillator elements 28, 29 are arranged in a specific location with respect to the blade, on the basis of this blade-specific contour. The first quartz oscillator element 28 is arranged such that a positioning (or reference) signal effected by a certain blade geometry—here the trombone edge 6 of the trombone duct—is generated by which the correct position of the positioning probe 24 on the turbine blade 2 is recorded. The second quartz oscillator element 29 is arranged at a distance to the first quartz oscillator element 28 adjusted to the blade geometry such that the longitudinal ultrasonic waves generated by it precisely covers the area of the blade root 4 in which cracks are likely to occur and which is to be inspected for crack formation.

In the following, a typical ultrasonic inspection of the turbine blades installed in a gas turbine engine using the above apparatus is described. The measuring apparatus proper, including the positioning probe 24 and the signal indicator 27 connected to this probe via a change-over switch 26, is calibrated prior to the performance of the inspection.

In preparation of the inspection, access to the fuel nozzles is first gained on the engine casing and then, upon removal of one fuel nozzle, to the turbine blades 1 via the combustion chamber 10. In addition, a rotating device (not shown) is fitted to the engine, enabling the rotor disk with the turbine blades 1 arranged on its circumference to be advanced and one turbine blade after the other to be inspected.

For performance of the ultrasonic inspection, it must also be ensured that the temperature in the area of the high-pressure turbine does not exceed 50° C. Therefore, a temperature measurement is performed after cooling the high-pressure turbine module. For this purpose, a temperature sensor (not shown) is fitted to the manipulator 15 with the miniature camera 16 which slightly protrudes beyond the camera. Watching the pictorial representation on the screen 18, the manipulator 15 with the miniature camera 16 and the temperature sensor are fed through the combustion chamber 10 and between two stator vanes to the turbine blades 1 of the first high-pressure turbine stage. The temperature sensed there on a platform 3 is shown outside of the engine on a display unit (not shown) connected to the temperature sensor. If necessary, the engine must be cooled down further and the temperature measurement repeated.

For the inspection, the supply line 19 connected to the container 20 is attached to the flexible first manipulator 15 fitted to the miniature camera 16. Subsequently, the first manipulator 15 so prepared and the second manipulator 23 with the positioning probe 24 fitted to its end are moved to the first high-pressure turbine stage by manually operating the associated control units 17 or 25, respectively, watching the screen 18. The tip of the supply line 19 protruding beyond the miniature camera 16 is placed on that part of the surface of the platform 3 of the respective turbine blade 1 on which the positioning probe 24 is later to be positioned to apply couplant 22 to the platform 3 in a locally and quantitatively controlled manner by operating the metering piston 21 of the metering container 20, and watching the operation with the miniature camera 16.

The miniature camera 16 is then retracted slightly and the positioning probe 24 positioned on the leading edge 2a and the pressure side 2b of the airfoil 2 with its contoured side face 24a and on the platform 3 with its contoured bottom face 24b. However, the correct position of the positioning probe 24 is only reached if, in the switch position "T" of the change-over switch 26, a reference signal (positioning signal $S_P$) reflected by the trombone edge 6 of the trombone duct (trombone) is received by the first quartz oscillator element 28 and shown on the display 30 of the signal indicator unit 27 (crack detector). The positioning signal $S_P$ is shown in a certain zone of the graph in FIG. 7a. The longitudinal ultrasonic waves generated by the second quartz oscillator element 29 now cover precisely the area of the blade root 4 in which cracks are likely to occur. If such a crack 9 exists, the longitudinal ultrasonic waves reflected by it will be received by the quartz oscillator element 29 and, after switching the change-over switch 26 to switch position "N", shown on the display 30 as flaw signal $S_F$. In the zone of the graph shown in FIG. 7b in which the positioning signal $S_P$ appeared before in switch position "T", a flaw signal $S_F$ will now be visible indicating a crack 9 in the blade root 4 of the turbine blade 1 under inspection. In this case, the free end of the supply line 19 attached to the first manipulator 15 is again moved close to the turbine blade 1 and the concave side (pressure side 2b) of the turbine blade 1 marked with couplant so that the blade can be specifically identified for repair. The damaged blade can also be marked in another manner.

In the manner described in the above, all other turbine blades 1 fitted to the circumference of the rotor disk are now inspected for the presence of possible discontinuities in the blade root 4. Upon retraction of the manipulator 23 with positioning probe 24 and the manipulator 15 with miniature camera 16 and supply line 17 for the couplant, the rotor disk is advanced by means of the above-mentioned drive unit such that the next turbine blade can be inspected. If a turbine blade 1 is flawless in the respective crack-susceptible area 8, no crack signal will, as shown in FIG. 7c, be displayed in switch position "N" if a positioning signal $S_P$ according to FIG. 7a was generated before in switch position "T".

List of Reference Numerals

1 Turbine blade, component
2 Airfoil
2a Leading edge
2b Pressure side
3 Platform
4 Blade root
5 Cooling air duct
6 Trombone edge, geometrical contour
7 Cooling duct in 2
8 Crack-susceptible/critical area of 4
9 Crack in 8
10 Combustion chamber
11 Stator vanes
12 Combustion chamber outer casing
13 Opening in 12
14 Burner sleeve in 10
15 Flexible first manipulator
16 Miniature camera
17 First control unit
18 Screen
19 Supply line
20 Metering container
21 Metering piston
22 Couplant
23 Second manipulator
24 Positioning probe
24a Side face of 24
24b Bottom face of 24
25 Second control unit
26 Change-over switch
27 Signal indicator unit, crack detector
28 First quartz oscillator element for reference signal
29 Second quartz oscillator element for flaw signal
30 Display of 27

What is claimed is:

1. A method for non-destructive testing of components of gas turbine engines made of monocrystalline materials for the presence of cracks in a certain, critical area of a component upon expiry of a specific operating time, comprising:
   generating a reference signal, in an installed state of the components in an engine, on a component-specific geometrical contour adjacent to the critical area by use of first longitudinal ultrasonic waves for fine-positioning and, upon availability of the reference signal,
   emitting second longitudinal ultrasonic waves positionally correct at a local distance from the first ultrasonic waves, corresponding to the location of the critical area to cover the critical area and produce a flaw signal in the event of a crack formation in the critical area,
   with the first and second ultrasonic waves being previously rough-positioned by use of an ultrasonic probe form-fitted to an outer contour of the components under camera-visual control.

2. A method in accordance with claim 1, wherein defective components are given a marking immediately upon detection of discontinuities.

3. A method in accordance with claim 2, wherein a couplant used for transmission of the first and second ultrasonic waves into the component is used for the marking.

4. A method in accordance with claim 3, wherein access to the components and rough-positioning and marking within the engine are performed under visual control using a miniature camera.

5. A method in accordance with claim 4, wherein the non-destructive testing is performed at a component temperature below 50° C.

6. A method in accordance with claim 5, wherein the temperature of the components is measured in the engine and the components are cooled, if necessary.

7. A method in accordance with claim 1, wherein access to the components and rough-positioning and marking within the engine axe performed under visual control using a miniature camera.

8. A method in accordance with claim 1, wherein the non-destructive testing is performed at a component temperature below 50° C.

9. A method in accordance with claim 8, wherein the temperature of the components is measured in the engine and the components are cooled, if necessary.

10. An apparatus for performance of the method according to claim 1, comprising:
a positioning probe including:
at least one face contoured to form-fit a surface contour of an area of the components to be inspected for rough-positioning of the first and second ultrasonic waves,
a first quartz oscillator element arranged relative to a geometrical contour in or on the respective component for generation of longitudinal ultrasonic waves and for reception of a reference signal reflected by the contour for fine-positioning of the positioning probe, and
a second quartz oscillator element arranged at a certain distance from the first quartz oscillator element for generation of longitudinal ultrasonic waves in the critical area of the respective component to be inspected and for reception of a flaw signal reflected by a crack existing in the respective area,
a flexible manipulator to which the positioning probe is connected,
a control unit positioned outside of the engine to which the flexible manipulator is connected for moving the manipulator and the positioning probe in various directions,
a signal indicator unit to which the flexible manipulator is connected, having a display and a change-over switch for indication of either the reference signal or the flaw signal reflected on a crack, and
a miniature camera attached to a further flexible manipulator and having a control unit for movement control of the further flexible manipulator and the miniature camera,
a screen attached to the end of the further flexible manipulator located outside of the engine, and
a supply line and a metering container for supplying a couplant connected to the further flexible manipulator.

11. An apparatus in accordance with claim 10, wherein the metering container includes a metering piston and a screw spindle for adjusting the metering piston.

12. An apparatus in accordance wit claim 11, wherein a free end of the supply line protrudes beyond the miniature camera to allow visual observation through the miniature camera of the application of the couplant to the component.

13. An apparatus in accordance with claim 12, and further comprising a temperature sensor connected to the further flexible manipulator having a free end which protrudes beyond the miniature camera and an end located outside of the engine which is connected to a temperature measuring unit.

14. An apparatus in accordance with claim 10, wherein a free end of the supply line protrudes beyond the miniature camera to all6w visual observation trough the miniature camera of the application of the couplant to the component.

15. An apparatus in accordance wit claim 10, and further comprising a temperature sensor connected to the further flexible manipulator having a free end which protrudes beyond the miniature camera and an end located outside of the engine which is connected to a temperature measuring unit.

* * * * *